(12) United States Patent
Weston

(10) Patent No.: US 8,343,177 B2
(45) Date of Patent: Jan. 1, 2013

(54) TREPHINE WITH TRANSPARENT CASING

(76) Inventor: Philip Douglas Weston, Ledyard, CT (US)

(*) Notice: Subject to any disclaimer, the term of this patent is extended or adjusted under 35 U.S.C. 154(b) by 259 days.

(21) Appl. No.: 12/592,479

(22) Filed: Nov. 25, 2009

(65) Prior Publication Data

US 2010/0152754 A1 Jun. 17, 2010

(30) Foreign Application Priority Data

Nov. 27, 2008 (GB) .................................. 0821640.0

(51) Int. Cl.
*A61F 9/007* (2006.01)
(52) U.S. Cl. ........................................................ 606/166
(58) Field of Classification Search .................. 606/107, 606/161, 166, 171, 172, 184, 167; 623/6.12
See application file for complete search history.

(56) References Cited

U.S. PATENT DOCUMENTS

| | | | | | |
|---|---|---|---|---|---|
| 2,473,968 | A | * | 6/1949 | Paton | 606/166 |
| 4,429,696 | A | | 2/1984 | Hanna | |
| 4,744,362 | A | | 5/1988 | Grundler | |
| 4,947,871 | A | * | 8/1990 | Grieshaber | 128/898 |
| 5,318,044 | A | * | 6/1994 | Kilmer et al. | 128/898 |
| 5,938,674 | A | * | 8/1999 | Terry | 606/166 |
| 6,458,141 | B1 | * | 10/2002 | Peyman | 606/166 |
| 2002/0013579 | A1 | * | 1/2002 | Silvestrini | 606/32 |
| 2006/0287663 | A1 | | 12/2006 | Gayheart et al. | |
| 2007/0083221 | A1 | * | 4/2007 | Carda | 606/166 |
| 2008/0140103 | A1 | * | 6/2008 | Gayheart et al. | 606/166 |

OTHER PUBLICATIONS

R. Michael Duffin, et al., "Analysis of the Hessburg-Barron Vacuum Trephine," Ophthalmic surgery, Jan. 1984, pp. 51-54, vol. 15, No. 1.

* cited by examiner

*Primary Examiner* — Ryan Severson
*Assistant Examiner* — Rachel S Papeika
(74) *Attorney, Agent, or Firm* — Ira S. Dorman

(57) ABSTRACT

Trephine apparatus has an outer casing with means defining a substantially cylindrical passage, or aperture, opening at a substantially circular lower end element, and an inner, substantially cylindrical tube having a bore opening at a substantially circular lower end element, the lower end element of the inner tube being upwardly spaced, or recessed, from the lower end element of the outer casing within the passage. A substantially cylindrical trephine blade is mounted within the bore of the inner tube by means that is so constructed as to enable raising and lowering of the blade relative to the end elements of the outer casing and the inner tube. At least a lower end element of the outer casing, or a base portion including it, is made of a non-opaque material, enabling edge-on viewing of the basal element of the inner tube and the blade, such as by use of a microscope, without parallax between the blade and the basal element of the inner tube. The zero position of the blade can be set easily and highly accurately, in a manner that is not possible with existing vacuum trephine assemblies.

18 Claims, 4 Drawing Sheets

TREPHINE WITH TRANSPARENT CASING

The present invention relates to a trephine for use in ophthalmic surgery, particularly but not exclusively in the field of corneal graft surgery and/or penetrating keratoplasty.

BACKGROUND OF THE INVENTION

A trephine is a surgical instrument having a cylindrical blade, and particular types of trephine are used in ophthalmic surgery to cut buttons from donor corneal grafts, and also to cut away diseased sections of a patient's cornea. These trephines have ultra-sharp blades so as to reduce the risk of damage to the cornea when cutting.

Typical corneal trephines are known, for example, from U.S. Pat. No. 4,319,575 and U.S. Pat. No. 2,473,968, the disclosures of which are hereby incorporated into the present application by reference.

A more recent development in this area is the Hessburg-Barron vacuum trephine, available from Barren Precision Instruments, LLC. This comprises an outer, generally cylindrical casing with an annular base and an inner, cylindrical tube of slightly smaller diameter than the outer casing and also having an annular base, slightly recessed from the annular base of the outer casing. This allows the base of the casing to be placed on the curved epithelium of a cornea, with the recessed base of the tube also resting on the epithelium as a result of the convex curvature of the cornea. When a vacuum is applied to the cylindrical space between the outer casing and the inner tube, the casing becomes attached to the epithelium by suction, thereby preventing movement between the casing and the cornea. A cylindrical trephine blade is mounted inside the inner tube and provided with a screw mechanism so as to allow the blade to be raised and lowered within the inner tube. A spoked wheel is provided at an end of the trephine remote from the base so as to allow the amount the blade is raised and lowered to be determined by a number of turns or fractions of turns of the spoked wheel.

In use, the trephine is examined under an operating microscope and the spoked wheel is turned until the blade of the trephine is aligned with the base of the inner tube, this being the zero position. The blade is then retracted by turning the spoked wheel anticlockwise so as to ensure that the blade does not touch the cornea when the vacuum trephine assembly is placed on the epithelium with both the base of the casing and the base of the inner tube contacting the epithelial surface of the cornea. If the blade is not sufficiently retracted, a vacuum between the casing, the inner tube and the cornea cannot be obtained.

A vacuum is then applied to the cylindrical space between the casing and the inner tube, for example by using a syringe with a flexible tube connected to the annular space.

Once a good vacuum seal has been obtained and the assembly is fixed to the cornea by suction, the spoked wheel is rotated clockwise until the blade touches the cornea (this will generally be slightly behind the zero position due to the convex curvature of the cornea), and cutting then starts by continuing to rotate the spoked wheel a desired number of turns. In currently available embodiments of the Hessburg-Barron vacuum trephine, each complete revolution of the spoked wheel raises or lowers the blade of the trephine by approximately 0.25 mm relative to the casing and the inner tube. At the desired depth of cut, the vacuum is released by operating the syringe appropriately, and the trephine is then lifted from the patient's eye.

While operation of the vacuum trephine has been described with reference to a living patient, it may also be used to cut a button from a donor corneal graft harvested from a cadaver and mounted on an artificial anterior chamber.

A significant problem associated with existing vacuum trephines is that the zero position of the blade can be difficult to set accurately. This is because the casing and the inner tube are made of surgical grade stainless steel or the like, and are thus opaque. Because the zero position of the blade is when it is level with the base of the inner tube, which is recessed from the base of the casing, it is not possible to use a microscope to get a square-on view of the blade relative to the base (lower end element) of the inner tube. Instead, it is necessary to observe the base of the inner tube and the blade at an angle, which leads to parallax errors.

BRIEF SUMMARY OF THE DISCLOSURE

According to the present invention, there is provided a trephine apparatus comprising an outer casing with means defining a substantially cylindrical aperture or passage opening at a substantially circular lower end, or basal, element having a circumferential end or edge surface that may be annular or arcuate in cross section; an inner, substantially cylindrical tube having a bore opening at a substantially circular lower end, or basal, element having a circumferential end or edge surface that may be annular or arcuate in cross section, the lower end element of the inner tube being proximate to but recessed, or spaced upwardly, from the lower end element of the outer casing within the passage; and means for mounting a substantially cylindrical trephine blade within the bore of the inner tube and being so constructed that the blade can be raised and lowered thereby, relative to the lower end elements of the outer casing and the inner tube, at least the lower end element of the outer casing being made of a non-opaque (i.e., substantially transparent or translucent) material.

The lower end element of the inner tube is preferably spaced or recessed from the lower end element of the outer casing by a degree sufficient to allow the circumferential end surfaces of both elements to contact the curved corneal surface of an eyeball when placed appropriately thereupon. A vacuum or partial vacuum may then be applied to a volume, or space, defined between the outer casing and the inner tube, for example by way of a suction pump connected by a flexible tube, hose, or the like, and ports and air-tight fittings, to communicate with the space and thereby to cause the trephine apparatus to become releasably attached to the surface of the eyeball when in position.

Preferably, the non-opaque material will be made of a substantially transparent surgical grade plastics material, such as a polycarbonate (e.g. Makrolon®) or the like.

In some embodiments, a longer section of a base portion of the outer casing that includes its lower end element, or the entire outer casing, is made of a substantially non-opaque material such as a transparent plastics material. In other embodiments only the lower end element, or the longer section of the base portion of the outer casing (i.e., the element or section thereof that surrounds the lower end, or basal, element of the inner tube) is made of a non-opaque material. The inner tube, or a lower end element or section thereof, may also be made of a non-opaque material.

The novel construction described provides the advantage that the basal element of the inner tube, and the blade, can be viewed (such as with a microscope) edge-on through the non-opaque material and without parallax between the blade and the basal element of the inner tube. This in turn allows the zero position of the blade to be set easily and highly accurately, in a manner not possible with existing vacuum trephine assemblies.

The trephine blade is preferably provided at one end (i.e., the lower end) of a substantially cylindrical holder, the holder being dimensioned and configured to fit rotatably inside the inner tube. The holder may be provided with screw thread means adapted to engage corresponding screw thread means, normally provided on an inner surface of the inner tube, so as to allow raising and lowering of the blade by rotating the holder clockwise or anticlockwise.

An end of the holder remote from the blade may be provided with a spoked wheel or other means for facilitating rotation of the holder and providing easy reference to a surgeon as to how many turns, or fractions of turns, the holder is rotated during operation.

The holder and/or the means for facilitating rotation may be made of a surgical grade metal or plastics material, as may the inner tube.

An outside surface of the outer casing is preferably provided with means for facilitating gripping thereof by a surgeon during use. For example, the outside surface may be roughened or ridged, or may include at least one pair of opposed projecting members having, respectively, finger and thumb rests. The projecting members, where provided, may project from the outer casing or, in some embodiments, from the inner tube.

In addition to providing good edge-on lateral visibility of the basal element of the inner tube and the blade, the use of non-opaque, preferably substantially transparent plastics materials (as opposed to opaque metal materials, for example) in the outer casing (and optionally, the inner tube) allows the assembly to be made less heavy, and potentially assists in positional stability by lowering the centre of mass of the trephine apparatus (since plastics materials generally have lower density than metallic materials). Moreover, modern plastics moulding techniques can allow a greater degree of manufacturing accuracy to be achieved than traditional metal milling techniques.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

For a better understanding of the present invention and to show how it may be carried into effect, reference shall now be made by way of example to the accompanying drawings, in which.

DETAILED DESCRIPTION OF THE INVENTION

Figure 1:
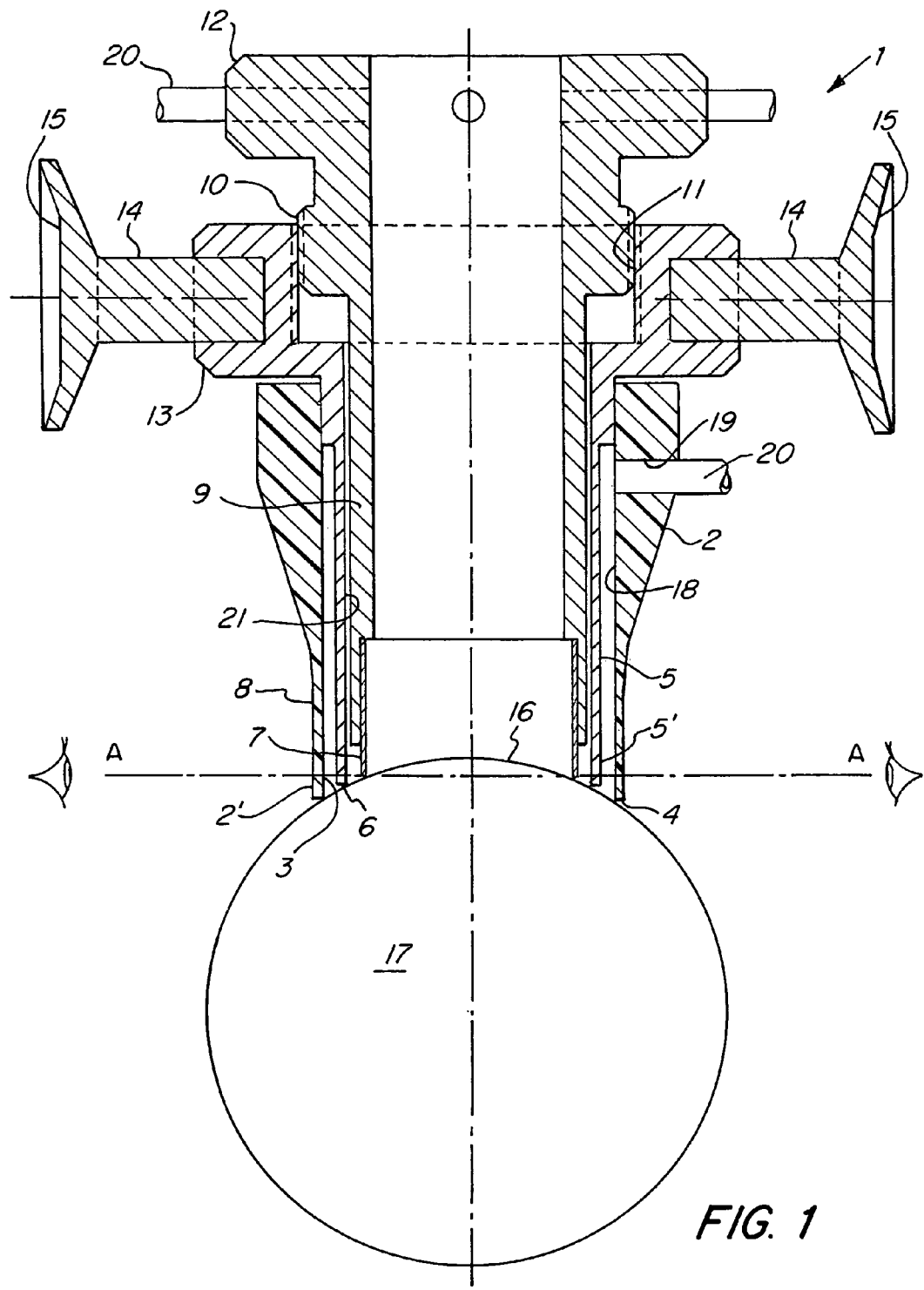
FIG. 1 shows an embodiment of the present invention in cross section resting on an eyeball.

With reference to FIG. 1, there is shown a trephine apparatus 1 embodying the invention and comprising an outer casing 2 with means defining a substantially cylindrical aperture or passage 3 and having a substantially annular base or end surface 4. An inner, substantially cylindrical tube 5, having a substantially annular base or end surface 6, is mounted within the passage 3 of the outer casing 2. The surface 6 of the base element 5' of the inner tube 5 is recessed (spaced upwardly) from the surface 4 of the base element 2' of the outer casing 2 within the aperture 3. A substantially cylindrical trephine blade 7 is located within the bore 21 of the inner tube 5 and is configured and constructed such that the blade 7 can be raised and lowered relative to the base elements 2', 5' of the outer casing 2 and the inner tube 5 respectively. At least the basal element 2' or a base portion 8 (which may be considered to comprise the cylindrical lower section, as illustrated in FIG. 1) of the outer casing 2 is made of a non-opaque material (e.g., a material that is substantially transparent or translucent to visible light), although in preferred embodiments the entire outer casing 2 will be made of such a material; most desirably, the non-opaque material used will be substantially visually transparent.

Because at least the element 2' or the portion 8 of the casing 2 is transparent, or at least non-opaque, it is possible to observe the position of the blade 7 directly along sight line A-A without parallax. It is noted that the sight line A-A, in the illustrated embodiment, extends through the basal element 5' of the inner tube 5 as well as through the non-opaque portion 8 of the outer casing 2. Firstly, however, it should be appreciated that the curvature of the corneal surface 16 is exaggerated, as depicted. But moreover, this feature may be accommodated either by forming the entire inner tube 5, or only the basal element 5' or a longer lower portion thereof, from a non-opaque material; or (when the inner tube is made of an opaque material) by setting the cutting depth of the trephine blade 7 in accordance with the distance it is caused to protrude beyond the lower surface 6 of the inner tube 5, i.e., by causing the sight line A-A to be a line through, or just below, the plane on which lower surface 6 of the inner tube resides. It should also be appreciated that, depending upon the nature of the cornea-contacting surfaces of the casing and tube end elements, only an outer edge of the lower element (rather than the entire contacting surface) might be visible along the sight line (as for example in the form depicted in FIG. 4).

The trephine blade 7 is mounted at one end (i.e., the lower end) of a substantially cylindrical holder 9, the holder 9 being dimensioned and configured to fit rotatably in the bore 21 of the inner tube 5. The holder 9 is provided with screw thread means 10 adapted to engage corresponding screw thread means 11 provided on an inner surface of a head portion the inner tube 5, so as to enable raising and lowering of the blade 7 by rotating the holder 9 clockwise or anticlockwise.

An end of the holder 9 remote from the blade 7 (i.e., the upper end) is provided with a spoked 20 or knurled wheel 12 or other means for facilitating rotation of the holder 9. This construction also provides ready reference for enabling a surgeon to determine how many turns, or fractions of turns, the holder 9 is rotated during operation. The holder 9 and/or the means 12 for facilitating rotation may be made of a surgical grade metal or plastics material, as may the inner tube 5.

An outside surface of the inner tube 5 is provided with means 13 for facilitating gripping thereof by a surgeon during use. In the illustrated embodiment, the means 13 takes the form of at least one pair of opposed projecting members 14 having, respectively, finger and thumb rests 15.

The basal element 5' of the inner tube 5 is recessed from the basal element 2' of the outer casing 2 by a degree sufficient to allow the edge surfaces 4, 6 of both elements to simultaneously contact the curved epithelial corneal surface 16 of an eyeball 17 when placed appropriately thereupon. A vacuum or partial vacuum may then be applied to the cylindrical space or volume 18, defined between the outer casing 2 and the inner tube 5, for example by way of a suction pump (not shown) connected by way of an air-tight fitting 20 that communicates with the space 18 by way of a port 19 through the casing 2, thereby to cause the trephine apparatus 1 to become releasably attached to the surface 16 of the eyeball 17 when in position.

Figure 2:
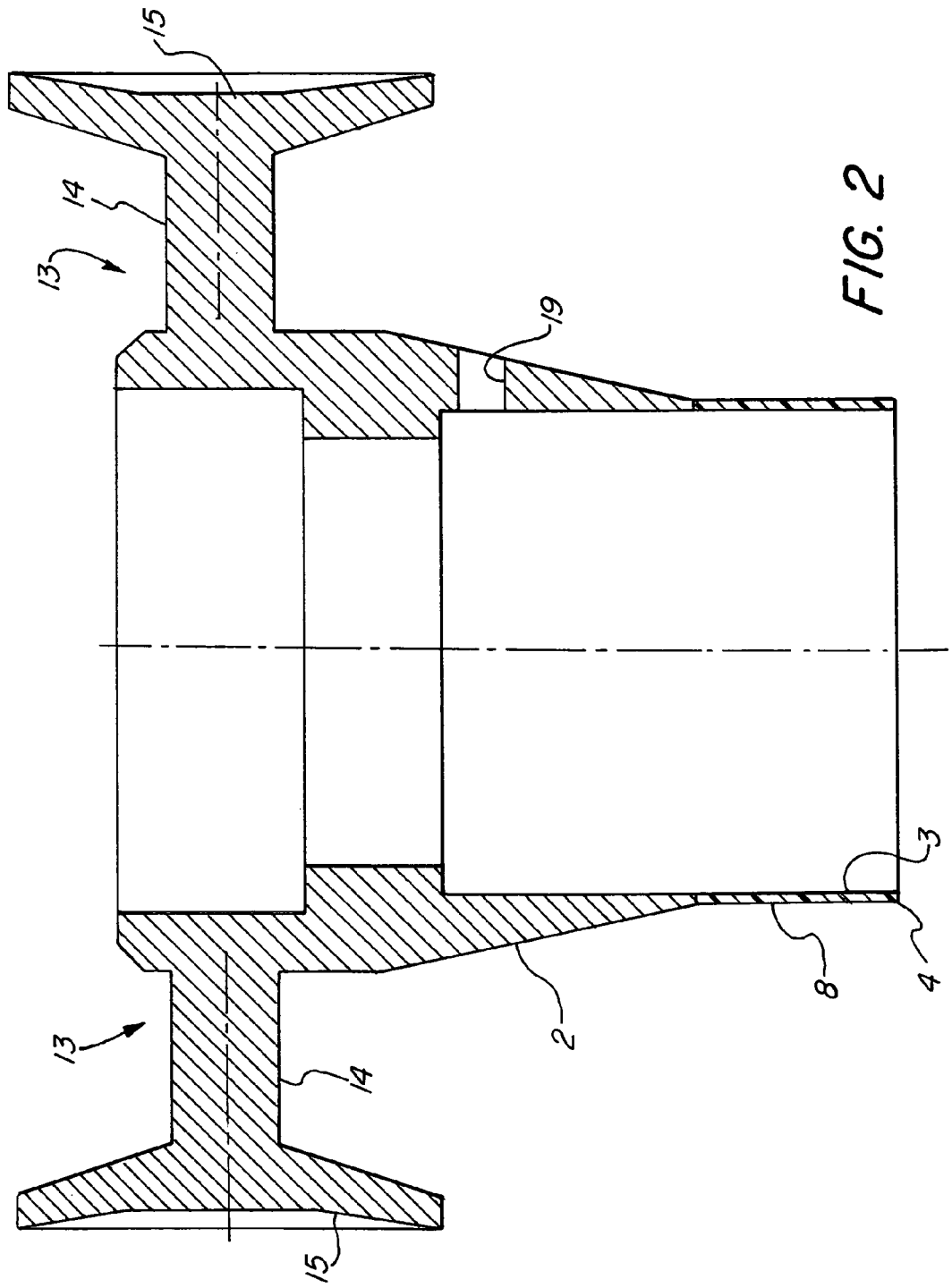
FIG. 2 shows a cross section through an outer casing of an alternative embodiment of the present invention.
Figure 3:
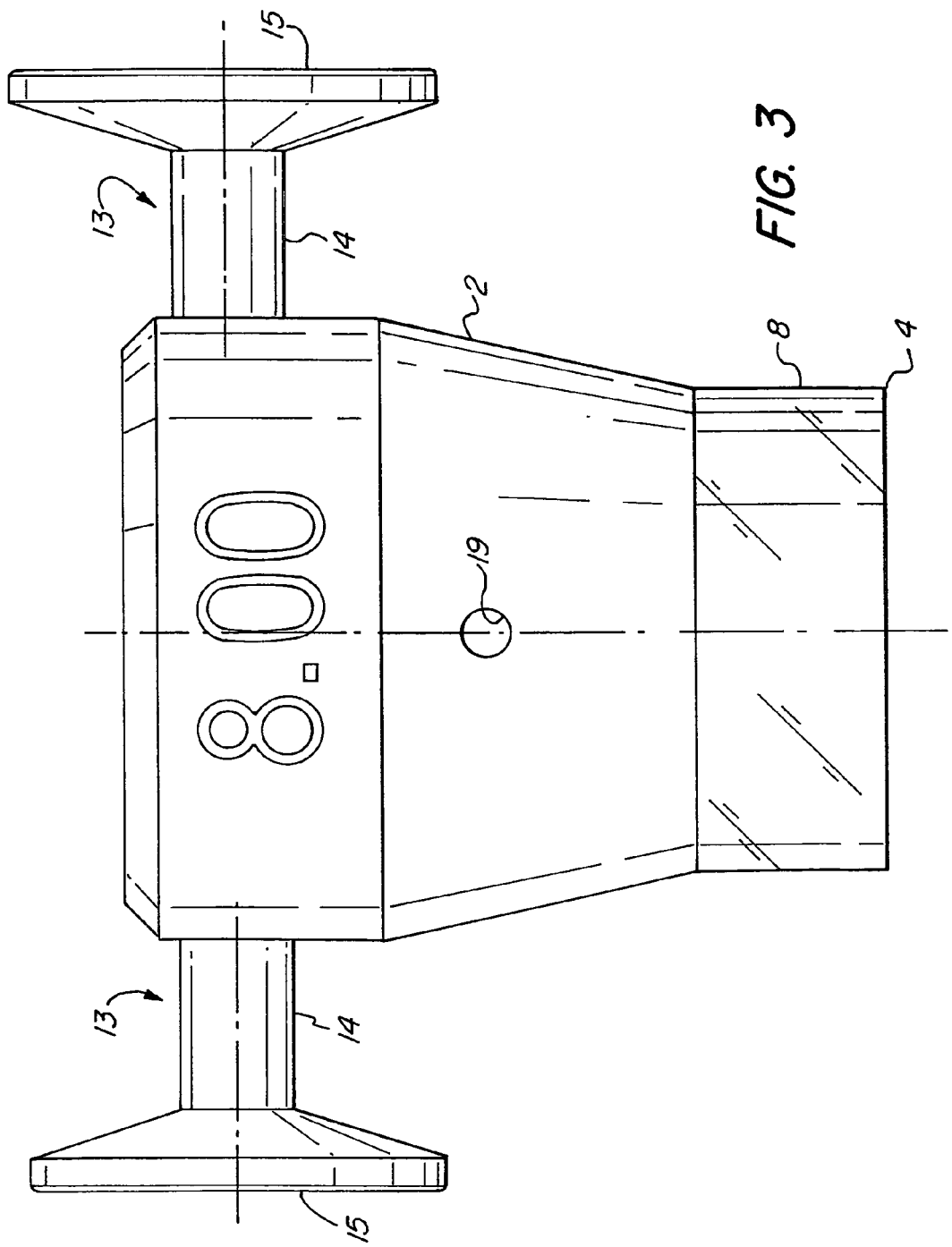
FIG. 3 shows a side elevation of the outer casing of FIG. 2.

FIGS. 2 and 3 show the outer casing 2 of an alternative embodiment, in which the projecting members 14 and rests 15 of the gripping means 13 are formed integrally with the outer casing 2. This is in contrast to the embodiment of FIG. 1, where the gripping means 13 are connected to the inner tube 5. The inner tube 5 and the holder 9 with its blade 7 are not shown in FIGS. 2 and 3.

Figure 4:
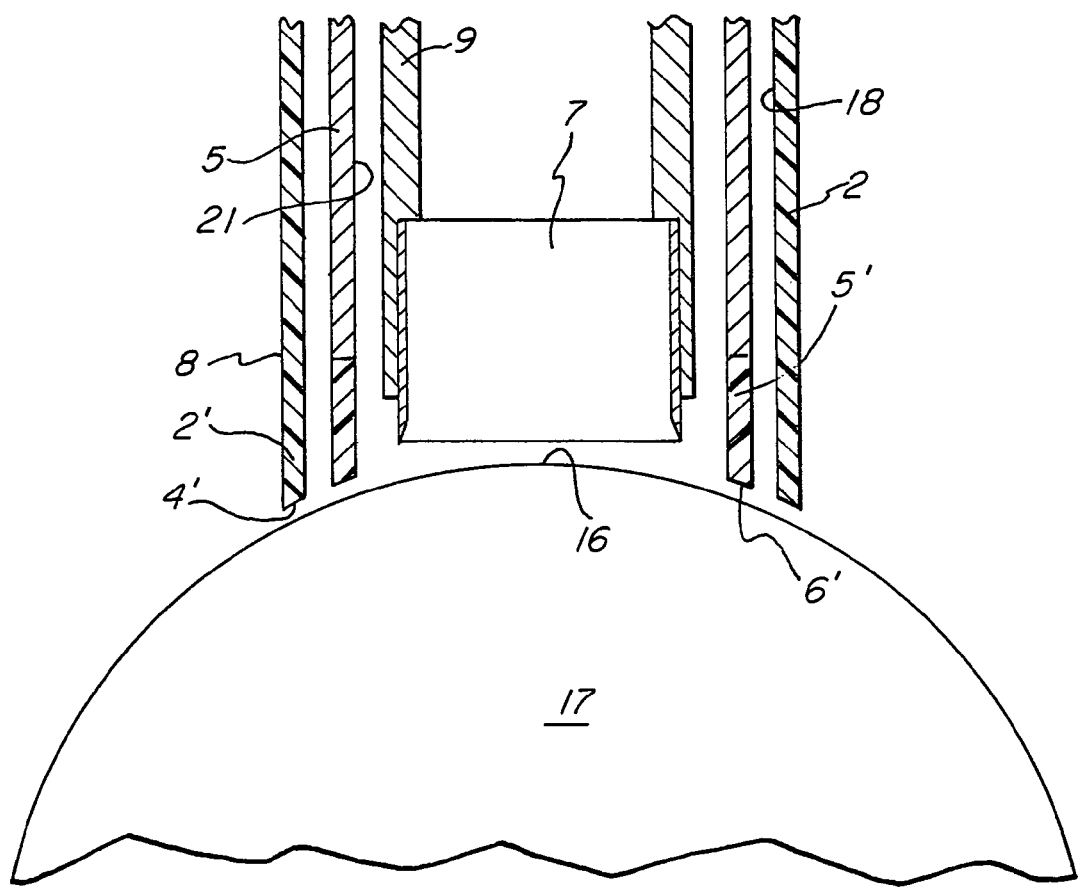
FIG. 4 shows an embodiment in which the circumferential basal end surfaces of the outer casing and inner tube are concave or arcuately recessed.

FIG. 4 diagrammatically illustrates apparatus embodying the invention in which the circumferential edge surfaces 4' and 6' of the lower or basal end elements 2', 5' of the outer casing 2 and inner tube 5, respectively, are concave (i.e., arcuately recessed in cross section). Surfaces 4' and 6' are thus configured to conform closely to the outer surface 16 of an eyeball 17 when in contact therewith.

As will be apparent from the foregoing description, the lower end or basal elements of the outer casing and inner tube generally surround the cutting edge of the trephine blade, and lie substantially in the plane of that edge or in planes parallel thereto, when the blade edge is closely proximate to, or in contact with, a corneal surface. Because the function of the non-opaque elements or portions is to provide visual access, it will be appreciated that considerable latitude, consistent with that function, is contemplated.

The invention claimed is:

1. A trephine apparatus comprising an outer casing having structure with a lower end and defining a substantially cylindrical passage opening at a substantially circular lower end element; an inner, substantially cylindrical tube disposed within the substantially cylindrical passage of the outer casing and having a bore opening at a substantially circular lower end element, the lower end element of the inner tube being proximate to, but spaced upwardly from, the lower end element of the outer casing; means for mounting a substantially cylindrical trephine blade within the bore of the inner tube, said inner tube and said means for mounting being so constructed that the blade can be raised and lowered in said bore of said inner tube by said means for mounting, relative to the lower end elements of the outer casing and the inner tube; and a substantially cylindrical trephine blade mounted by said means for mounting and terminating in a hollow, cylindrical cutting edge downwardly disposed, said blade being disposed within said bore of said substantially cylindrical tube, with said cutting edge thereof disposed upwardly of said substantially circular lower end element of said substantially cylindrical tube in the course of normal operation of said apparatus, at least a basal element at the lower end of the outer casing being made of a non-opaque material so as to enable edge-on observation of the zero position of the trephine blade cutting edge in the course of normal operation of said apparatus.

2. A trephine apparatus as claimed in claim 1, wherein the lower end element of the inner tube is spaced upwardly from the lower end element of the outer casing by a degree sufficient to allow surfaces on both of the lower end elements to simultaneously contact the curved corneal surface of an eyeball when placed appropriately thereupon 3. A trephine apparatus as claimed in claim 1, wherein a cylindrical space is defined between the outer casing and the inner tube, and wherein the apparatus additionally comprises means for placing the cylindrical space in fluid communication with a source of suction, thereby to allow the trephine apparatus to become releasably attached by suction to the corneal surface of an eyeball.

4. A trephine apparatus as claimed in claim 1, wherein the non-opaque material is substantially transparent or substantially translucent.

5. A trephine apparatus as claimed in claim 1, wherein the non-opaque material is a surgical grade plastics material.

6. The trephine apparatus of claim 5 wherein the plastics material is a polycarbonate resin.

7. A trephine apparatus as claimed in claim 1, wherein the entire outer casing is made of the non-opaque material.

8. A trephine apparatus as claimed in claim 1, wherein only a section of the basal element of the outer casing that includes the lower end element of the outer casing and that surrounds the lower end element of the inner tube is made of the non-opaque material.

9. A trephine apparatus as claimed in claim 1, wherein the means for mounting includes a substantially cylindrical holder dimensioned and configured to fit rotatably within the bore of the inner tube, the trephine blade being mounted at a lower end of the holder.

10. A trephine apparatus as claimed in claim 9, wherein the holder is provided with screw thread means and wherein corresponding screw thread means is provided on an inner surface of the inner tube, the screw thread means on the holder and on the inner tube being engaged with one another so as to enable raising and lowering of the blade by rotating the holder.

11. A trephine apparatus as claimed in claim 10, wherein an upper end portion of the holder is provided with a spoked wheel for facilitating rotation of the holder and providing easy reference to a surgeon for determining the number of turns, or fractions of turns, the holder is rotated during operation.

12. A trephine apparatus as claimed in claim 11, wherein an outside surface of the outer casing is provided with means for facilitating gripping thereof by a surgeon during use.

13. A trephine apparatus as claimed in claim 12, wherein the outside surface of the outer casing is provided with at least one pair of opposed projecting members having, respectively, finger and thumb rests.

14. A trephine apparatus as claimed in claim 1, wherein the inner tube is provided with at least one pair of opposed projecting members having, respectively, finger and thumb rests.

15. A trephine apparatus as claimed in claim 1, wherein the substantially circular lower end elements of the outer casing and the inner tube have circumferential edge surfaces that are either annular or of arcuate cross section.

16. The trephine apparatus as claimed in claim 15 wherein the circumferential edge surfaces are of arcuately, concavely recessed cross section.

17. The trephine apparatus of claim 1, wherein at least a basal element at the lower end of the inner tube is made of a non-opaque material.

18. A trephine apparatus comprising an outer casing having structure with a lower end and defining a substantially cylindrical passage opening at a substantially circular lower end element; an inner, substantially cylindrical tube having a lower end and being disposed within the substantially cylindrical passage of the outer casing and having a bore opening at a substantially circular lower end element, the lower end element of the inner tube being proximate to, but spaced upwardly from, the lower end element of the outer casing; and means for mounting a substantially cylindrical trephine blade, terminating in a downwardly disposed hollow, cylindrical cutting edge, within the bore of the inner tube, said means for mounting and said inner tube being so constructed that a blade so mounted can be raised and lowered by said means for mounting, relative to the lower end elements of the outer casing, so as to enable disposition of the blade entirely within said bore of said inner tube, and at least a basal element at the lower end of the outer casing and at least a basal element at the lower of the inner tube being made of a non-opaque material so as to enable observation, through said basal elements, of the cutting edge of a trephine blade so mounted by said means for mounting and disposed within said bore of said inner tube.

* * * * *